United States Patent [19]
Tarragano

[11] Patent Number: 4,908,878
[45] Date of Patent: Mar. 20, 1990

[54] DISPOSABLE, ONE-PIECE LIGHT SHIELD

[76] Inventor: Morris Tarragano, 160 E. 48th St., New York, N.Y. 10017

[21] Appl. No.: 304,322

[22] Filed: Jan. 31, 1989

[51] Int. Cl.⁴ .............................................. A61F 9/04
[52] U.S. Cl. ................................................ 2/15; 2/9; 128/206.13
[58] Field of Search ........................ 2/9, 10, 11, 12, 15

[56] References Cited

U.S. PATENT DOCUMENTS

| | | | |
|---|---|---|---|
| 2,517,864 | 8/1950 | Fulton | 2/15 X |
| 2,537,768 | 1/1951 | LaPorte | 2/15 |
| 2,543,104 | 2/1951 | Golding | 2/15 X |
| 2,671,898 | 3/1954 | Wade | 2/15 |
| 4,039,711 | 8/1977 | Newman | 428/286 |
| 4,084,585 | 4/1978 | Venaleck | 2/206 X |
| 4,157,719 | 6/1979 | DeWoskin | 128/291 |
| 4,195,629 | 4/1980 | Halford | 128/206.13 |
| 4,327,448 | 5/1982 | Lunt | 2/404 |
| 4,382,303 | 5/1983 | Lunt | 2/69.5 X |
| 4,411,263 | 10/1983 | Cook | 2/15 X |
| 4,745,636 | 5/1988 | Lunt | 2/402 |

FOREIGN PATENT DOCUMENTS 1433504 4/1976 United Kingdom .................... 2/9

Primary Examiner—Werner H. Schroeder
Assistant Examiner—Jeanette E. Chapman
Attorney, Agent, or Firm—Michael Ebert

[57] ABSTRACT

A disposable one-piece light shield adapted to excluse ambient light from the eyes of an adult wearer regardless of his head size. The shield is fabricated from a blank of soft, non-woven textile sheeting that is die cut to define a generally rectangular masking region and a pair of arched temple sections on either side of this region and integral therewith. The masking region which covers the eyes of the wearer and the portion of the forehead directly thereabove is provided at its midpoint on the lower edge thereof with an arcuate indentation to accommodate the nose bridge of the wearer. Each temple section is provided with an arched cut-out to create a loop that engages an ear of the wearer to retain the masking region in place, whereby to put on the light shield, the wearer has merely to slip the loops over his ears.

4 Claims, 1 Drawing Sheet

DISPOSABLE, ONE-PIECE LIGHT SHIELD

BACKGROUND OF INVENTION

1. Field of Invention:

This invention relates to masks or light shields adapted to cover a wearer's eyes to exclude ambient light and thereby promote slumber, and more particularly to a disposable, one-piece device of this type.

2. Status of Prior Art:

There was no need for light shields before the modern era, for then working and sleeping habits and the hours assigned thereto were dictated by the sun's trajectory, so that one generally worked during the day and slept at night. The concept of a night shift is of modern origin, for the strong artificial illumination necessary for this purpose represents a relatively recent advance. Also unthinkable before the modern era was air travel that traversed time zones at such high speeds as to foreshorten the night and make it necessary to sleep under daylight conditions.

Adequate sleep is essential to well being, for without sleep one is deprived of the regenerative process which then takes place. Yet the modern era has created an environment which is unnatural, for large segments of the population are required to work at night which nature has reserved for sleep, and to sleep during daylight hours intended for human activity. And travellers often have no choice but to sleep under daylight conditions.

The human sensory system is not shut down during sleep, but remains alert in a standby state to protect the sleeper. Thus a sleeper will be awakened by a loud noise; for even in deep sleep his ears are highly sensitive to sound. While the amount of ambient light impinging on the eyes is sharply reduced when the eyelids are closed, because of the eye's extreme sensitivity to light, the closed eyes remain responsive to ambient light. It is for this reason that most people find it difficult to take a siesta or to enjoy prolonged sleep under daylight conditions or when the lights in a bedroom are turned on.

Because sleep has restorative power, adequate sleep is particularly important to one who is recovering from an illness or a surgical procedure. Indeed, one therapeutic technique that is reputed to be highly beneficial is to induce prolonged sleep in a patient for a period far greater than the normal 7 or 8 hour span.

Yet in modern hospitals patients are often deprived of adequate sleep. The need to monitor around the clock a patient's temperature, pulse rate, blood pressure and other variables that reflect the patient's condition interferes with sleep, for the attending nurse in a ward occupied by several patients may find it necessary to turn on certain bed lights during night sleeping hours and thereby disturb the sleeping patients. Typically, with a post-operative patient, lights are kept on all night so as to afford immediate staff access to a patient in need, to the discomfort of the patient's roommates.

In order, therefore, to cope with these conditions and to provide means to exclude ambient light from a person's eyes to permit him to sleep soundly during the day or in other situations where the prevailing light is such as to frustrate sleep, various light shields have been developed which are formed of fabric materials and are now commercially available.

These light shields or masks are effective to the extent that they all function to block ambient light and are suitable for travel, at home, at the beach or wherever the conditions are such as to require light shielding. Yet they all suffer from certain practical drawbacks. These can best be appreciated in the context of a general hospital having hundreds, if not thousands, of patients occupying beds, or in a nursing home where similar conditions prevail.

The first hospital requirement is that the light shield be sterile and therefore not a source of infection. It is a simple matter to sterilize a fabric light shield. But once this shield is worn by a patient, it is no longer sterile and must be discarded and not reused. In order for it to be practical for a hospital to supply patients with disposable, sterile light shields, the cost per shield must be very low, which is not true of existing fabric light shields. And finally, it must be easy for the patient or for the nurse to attach the shield to the patient's head. Existing non-disposable light shields which include adjustable headbands must be adjusted to the head size of the wearer, and this represents a practical disadvantage.

The above practical requirements are not limited to hospitals, for should an airline or a hotel wish to supply passengers or guests with disposable, low cost, sterile light shields, existing fabric light shields do not satisfy these requirements.

With these requirements in mind, let us now consider a typical commercially-available light shield. This shield is made of satin or rayon facing sheets covering a padded core and provided with a fabric rim or frame which is also padded, the general shape of this shield being similar to that of one-piece plastic sunglasses.

In order to hold this shield or mask on the wearer's head, it is provided at either end with ribbons or elastic straps and a buckle or clasp of some sort so that the joined straps can be adjusted to the wearer's head size.

The cost of the fabrics which make up this shield and the sewing operations for assembling the shield are such as to make this shield fairly costly. And while it is possible to sterilize this fabric light shield so that when it is put on it is then in sterile condition, once used it ceases to be sterile. But a hospital or airline cannot afford to provide a patient or passenger, each time the need arises, with a fresh sterile mask if each mask costs a few dollars. Also, because these light shields are adjustable, under hospital or airline conditions, the shield may not be easy to put on so that it stays in place.

SUMMARY OF INVENTION

In view of the foregoing, the main object of this invention is to provide a disposable, one-piece light shield which is adapted to effectively exclude ambient light from the eyes of an adult wearer regardless of his head size.

More particularly, an object of this invention is to provide a light shield of the above type which is made entirely of soft, non-woven fabric sheeting that is low in lint and non-allergenic, so that it may be safely and comfortably worn over the eyes.

Also an object of the invention is to provide a light shield of the above type which is free of straps and other expedients for tying the shield to the head of the wearer, the shield being provided with temple loops that engage the ears of the wearer.

Yet another object of the invention is to provide a light shield of the above type which is die cut from a blank of non-woven sheeting whereby the cost of producing a light shield is in the penny range.

Briefly stated these objects are attained in a disposable one-piece light shield adapted to exclude ambient light from the eyes of an adult wearer regardless of his head size. The shield is fabricated from a blank of soft, non-woven textile sheeting that is die-cut to define a generally rectangular masking region and a pair of arched temple sections on either side of this region and integral therewith. The masking region which covers the eyes of the wearer and the portion of the forehead directly thereabove is provided at its midpoint on the lower edge thereof with an arcuate indentation to accommodate the nose bridge of the wearer. Each temple section is provided with an arched cut-out to create a loop that engages an ear of the wearer to retain the masking region in place, whereby to put on the light shield, the wearer has merely to slip the loops over his ears.

BRIEF DESCRIPTION OF DRAWINGS

For a better understanding of the invention as well as other objects and further features thereof, reference is made to the following detailed description to be read in conjunction with the accompanying drawings, wherein.

DESCRIPTION OF INVENTION

Figure 1:
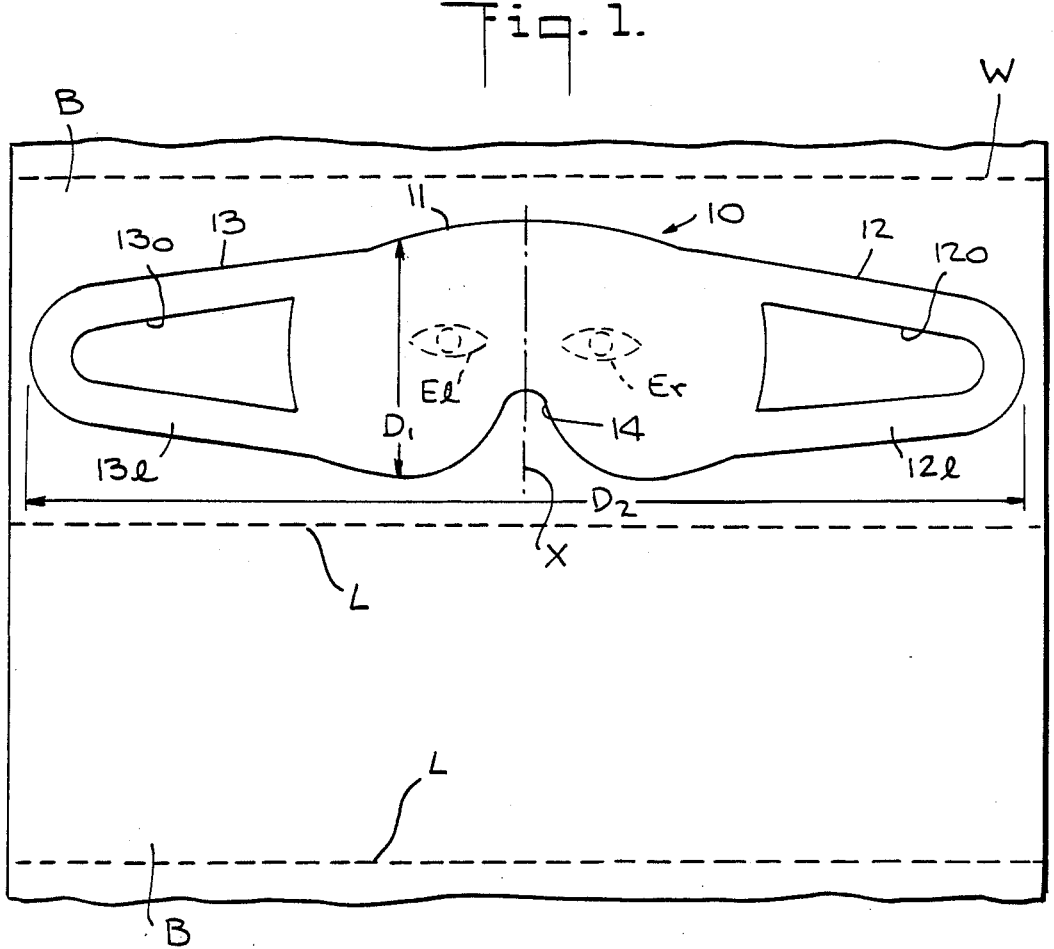
FIG. 1 is a plan view of a light shield in accordance with the invention.

Referring now to FIG. 1, there is shown a web W formed of non-woven fabric sheeting constituted by randomly dispersed, synthetic plastic fibers, the sheet being substantially impermeable to light rays so that it is effectively opaque. In practice, the fibers may be black or darkly colored to minimize light penetration.

Suitable for this purpose is a non-woven sheeting of the type known commercially under the trademark NEXUS, manufactured by Burlington Industries, this sheeting being formed of polyester fibers.

This non-woven polyester NEXUS material is lint free and soft, and it satisfies federal standards for non-flammability. It is non-toxic and non-allergenic, and is sterilizable. Because of the low cost of this material, it is expendable and therefore a light shield made therefrom is disposable.

Web 14 forms a series of like blanks B whose borders are indicated by dashed lines L, each blank being die-cut to create a light shield 10 in accordance with the invention. In practice, a stack of blanks B may be provided, such that when this stack is die-cut, one produces not a single light shield 10 but a multiplicity thereof.

When blank B is die-cut to create a light shield, it defines a generally rectangular masking region 11 and a pair of arched temple sections 12 and 13 on either side of this region integral with the masking region. The transverse axis X shown in FIG. 1 represents the midpoint of the light shield, and the eyes $E_l$ and $E_r$ on either side of this midpoint axis, shown in dashed lines, represent the eyes of the wearer, directly above which is a portion of the wearer's forehead. Hence when the light shield is worn, masking region 11 fully covers the eyes to block out light and the portion of the forehead directly above the eyes.

Masking region 11 is provided at its lower edge at a position bisected by midpoint axis X with an arcuate indentation 14 to accommodate the nose bridge of the wearer, thereby orienting this region with respect to the eyes.

Figure 2:
FIG. 2 is a perspective view of the light shield applied to the head of a wearer.

Temple sections 12 and 13 are each provided with an arched cutout $12_o$ and $13_o$, respectively, to create temple loops $12_l$ and $13_l$. These loops engage the ears of the wearer P, as shown in FIG. 2.

Because of the softness of the non-woven fabric material, the die cut edges thereof are not in the least sharp and therefore cause no discomfort to the wearer. In practice, we have found that a light shield which has a longitudinal size $D_2$ of $16\frac{1}{4}$ inches and a maximum transverse size $D_1$ of 4 inches in the eye zone of the masking region, is suitable for virtually all adults, regardless of their head size, and is therefore a universal light shield.

Figure 3:
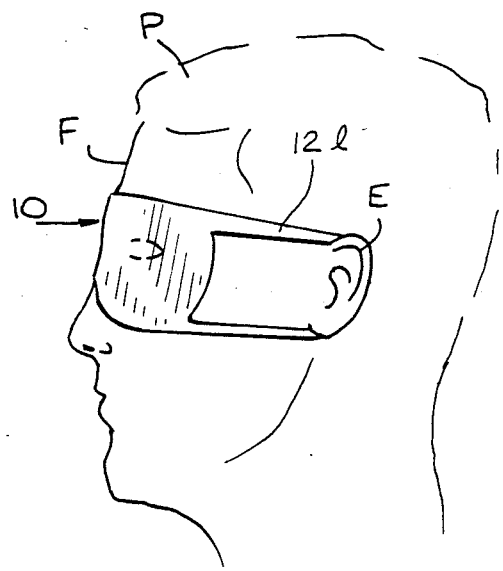
FIG. 3 illustrates the geometric relationship of the temple sections of the light shield to the ear and head of the wearer.

The reason it is possible to provide a non-adjustable, universal light shield that fits most adults regardless of their head sizes, is that, as shown in FIG. 3, the temple which is the flat area on either side of the head between the forehead F and the back of ear E does not vary to any great degree from person to person, whereas head sizes vary throughout a broad range. Thus two individuals who have different head sizes usually have temples of about the same length. Consequently, eyeglass frames having temple pieces of the same length can be worn by these individuals. In such eyeglass frames, the major adjustment that is normally made from wearer to wearer is the curvature of the crooked end of the temple piece which is altered to accommodate itself to the curvature of the wearer's ear. But in the present invention, the temple loops slip over all size ears.

Hence though prior art light shields, because they are tied to the head of the wearer, must be adjusted to the wearer's head size, with a light shield in accordance with the invention in which the loops are slipped over the wearer's ears, the mask is held in place regardless of the wearer's head size.

While there has been shown and described a preferred embodiment of a disposable, one-piece light shield in accordance with the invention, it will be appreciated that many changes and modifications may be made therein without, however, departing from the essential spirit thereof. Thus in order to provide a light shield having a relatively stiff frame, the periphery of the shield which follows the contours of the masking region and the temple loops may be ultrasonically welded to form a continuous border.

I claim:

1. A disposable, one-piece light shield adapted to exclude ambient light from the eyes of an adult wearer regardless of his head size, the shield being fabricated from sterile, non-allergenic, non-woven, soft textile sheeting that is die-cut to define a generally rectangular masking region and a pair of arched temple sections on either side of this region and integral therewith, the masking region which covers the eyes of the wearer and the portion of the forehead directly thereabove having at its midpoint on the lower edge thereof an arcuate indentation to accommodate the nose bridge of the wearer, each temple section having an arched cutout to create a temple loop that is engageable with an ear of the wearer to retain the masking region in place, whereby to put on the shield, the wearer has merely to slip the temple loops over the ears, each temple section lying flat against a temple of the wearer and having a length such that the temple loop fits over an ear of the wearer regardless of his head size within a broad range of head sizes, said die-cut sheeting having edges that are soft and therefore cause no injury or discomfort to the wearer.

2. A light shield as set forth in claim 1, wherein said sheeting is formed of randomly dispersed polyester fibers.

3. A light shield as set forth in claim 1, wherein said sheeting is colored to minimize light penetration.

4. A light shield as set forth in claim 1, wherein the periphery of said shield is ultrasonically welded to form a relatively stiff frame therefor.

* * * * *